United States Patent
Klein et al.

(10) Patent No.: US 9,090,567 B2
(45) Date of Patent: Jul. 28, 2015

(54) PROCESS FOR PREPARING IONIC LIQUIDS BY ANION EXCHANGE

(75) Inventors: Michael Klein, Reichenbach-Steegen (DE); Michael Siemer, Mannheim (DE); Diana Fürst, Ludwigshafen (DE); Günter Forster, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 437 days.

(21) Appl. No.: 13/418,828

(22) Filed: Mar. 13, 2012

(65) Prior Publication Data

US 2012/0238764 A1 Sep. 20, 2012

Related U.S. Application Data

(60) Provisional application No. 61/452,660, filed on Mar. 15, 2011.

(51) Int. Cl.
*C07D 233/56* (2006.01)
*C07D 233/64* (2006.01)
*C07D 213/20* (2006.01)
*C07D 233/58* (2006.01)

(52) U.S. Cl.
CPC .................... *C07D 233/58* (2013.01)

(58) Field of Classification Search
CPC ... C07D 233/56; C07D 233/64; C07D 213/20
USPC ........................ 548/335.1; 546/347
See application file for complete search history.

(56) References Cited

FOREIGN PATENT DOCUMENTS

| WO | WO 91/14678 | 10/1991 | |
|---|---|---|---|
| WO | WO 2005/021484 A2 | 3/2005 | |
| WO | WO 2005/113702 A1 | 12/2005 | |
| WO | WO 2008/043837 A1 | 4/2008 | |
| WO | WO 2009/027250 A2 | 3/2009 | |
| WO | 2009/059934 A1 * | 5/2009 | ........... C07D 233/58 |
| WO | WO 2009/059934 A1 | 5/2009 | |
| WO | WO 2009/074535 A2 | 6/2009 | |

OTHER PUBLICATIONS

Dinares et al, Green Chemistry (2009).*

* cited by examiner

*Primary Examiner* — Kamal Saeed
*Assistant Examiner* — Janet L Coppins
(74) *Attorney, Agent, or Firm* — Oblon, McClelland, Maier & Neustadt, L.L.P.

(57) ABSTRACT

Process for preparing salts $K^+ X^-$, where $K^+$ is an organic cation and $X^-$ is an anion, by anion exchange, wherein
a salt $K^+ Y^-$, where $K^+$ is as defined above and $Y^-$ is an organic anion having a carboxylate, sulfonate or sulfate group, is used as starting material and
$K^+Y^-$ is reacted with a hydrogen acid HX whose $pK_a$ is less than the $pK_a$ of the hydrogen acid HY and
after the reaction, the salt $K^+ X^-$ obtained and the hydrogen acid HY obtained are present in separate liquid phases.

16 Claims, No Drawings

PROCESS FOR PREPARING IONIC LIQUIDS BY ANION EXCHANGE

The invention relates to a process for preparing salts $K^+X^-$, where $K^+$ is an organic cation and $X^-$ is an anion, by anion exchange, wherein
- a salt $K^+Y^-$, where $K^+$ is as defined above and $Y^-$ is an organic anion having a carboxylate, sulfonate or sulfate group, is used as starting material and
- $K^+Y^-$ is reacted with a hydrogen acid HX whose $pK_a$ is less than the $pK_a$ of the hydrogen acid HY and
- after the reaction, the salt $K^+X^-$ obtained and the hydrogen acid HY obtained are present in separate liquid phases.

Ionic liquids are salts having a melting point below 100° C.; in particular, they are salts which are liquid at room temperature.

In general, the ionic liquids have an organic cation; mention may be made by way of example of an imidazolium cation. This organic cation makes a significant contribution to the salt having a low melting point and generally forms an ionic liquid with a wide variety of anions. The anions naturally have a strong influence on the use properties of ionic liquids, and different anions are accordingly suitable or preferred for different industrial applications.

In processes for preparing ionic liquids, the organic cation has therefore been produced first as a salt with an anion determined by the preparative process. From this salt, different ionic liquids can be obtained by anion exchange.

Such a process is known from, for example, WO 2005/021484. In this process, it is firstly necessary to prepare an imidazole. This imidazole is alkylated by means of a dialkyl carbonate, giving a salt made up of an imidazolium cation and a carbonate anion. When the carbonate anion is replaced by a different desired anion by addition of a hydrogen acid, the carbonate anion decomposes to form $CO_2$ and alkanol. To prepare an imidazolium salt having the desired anion, three steps are therefore necessary (preparation of imidazole—preparation of imidazolium carbonate—anion exchange).

WO 91/14678 describes a single-stage process for preparing imidazolium salts from an α-dicarbonyl compound, an aldehyde, an amine and an acid. An improved embodiment of this process is known from WO 2009/074535. In this process, a salt having an imidazolium cation is obtained directly in one step. Depending on the desired anion, there continues to be a necessity for anion exchange, as a result of which the process then has a total of two steps. In an anion exchange step, salts can, for example, be brought into contact with a suitable anion exchanger comprising hydroxide groups. In this way, the anion exchanger becomes loaded with the previous anions and the salts now comprise hydroxide groups as anions. Addition of a hydrogen acid then forms water and the salt having the anion of the hydrogen acid added.

It was an object of the present invention to provide a simple and effective process for preparing ionic liquids, e.g. imidazolium salts. In particular, ionic liquids having different anions should be able to be obtained easily by means of such a process.

We have accordingly found the process defined at the outset.

The process starts out from a salt $K^+Y^-$, where $K^+$ is an organic cation and $Y^-$ is an organic anion having a carboxylate, sulfonate or sulfate group.

The Cation $K^+$

Suitable organic cations are, in particular, organic compounds having heteroatoms such as nitrogen, sulfur, oxygen or phosphorus.

In particular, the organic cations are compounds having an ammonium group (ammonium cations), an oxonium group (oxonium cations), a sulfonium group (sulfonium cations) or a phosphonium group (phosphonium cations).

The cation is preferably an organic cation having at least one nitrogen atom.

In a particular embodiment, the organic cations are ammonium cations, which, for the present purposes, are
- nonaromatic compounds having a localized positive charge on the nitrogen atom, e.g. compounds having tetravalent nitrogen (quaternary ammonium compounds) or
- compounds having trivalent nitrogen, with one bond being a double bond, or
- aromatic compounds having a delocalized positive charge and at least one nitrogen atom, preferably from one to three nitrogen atoms, in the aromatic ring system.

Preferred organic cations are quaternary ammonium cations, preferably those having three or four aliphatic substituents, particularly preferably C1-C12-alkyl groups, which may optionally be substituted by hydroxyl groups, on the nitrogen atom.

Preference is likewise given to organic cations which comprise a heterocyclic ring system, with at least one nitrogen atom, preferably from one to three nitrogen atoms, being constituent of the ring system.

Possible ring systems are monocyclic, bicyclic, aromatic or nonaromatic ring systems. Mention may be made by way of example of bicyclic systems as are described in WO 2008/043837. The bicyclic systems of WO 2008/043837 are diazabicyclo derivatives, preferably made up of a 7-membered ring and a 6-membered ring, which comprise an amidinium group; mention may be made, in particular, of the 1,8-diazabicyclo[5.4.0]undec-7-enium cation.

Very particular preference is given to cations which comprise a heterocyclic ring system having one or two nitrogen atoms as constituent of the ring system.

Possible organic cations of this type are, for example, pyridinium cations, pyridazinium cations, pyrimidinium cations, pyrazinium cations, imidazolium cations, pyrazolium cations, pyrazolinium cations, imidazolinium cations, thiazolium cations, triazolium cations, pyrrolidinium cations and imidazolidinium cations. These cations are, for example, mentioned in WO 2005/113702. If it is necessary for a positive charge on the nitrogen atom or in the aromatic ring system, the nitrogen atoms are in each case substituted by a hydrogen atom or an organic group having generally not more than 20 carbon atoms, preferably a hydrocarbon group, in particular a C1-C16-alkyl group, in particular a C1-C10-alkyl group, particularly preferably a C1-C4-alkyl group.

The carbon atoms of the ring system can also be substituted by organic groups having generally not more than 20 carbon atoms, preferably a hydrocarbon group, in particular a C1-C16-alkyl group, in particular a C1-C10-alkyl group, particularly preferably a C1-C4-alkyl group.

Particularly preferred ammonium cations are quaternary ammonium cations, imidazolium cations, pyrimidinium cations and pyrazolium cations.

The organic cation is particularly preferably an imidazolium cation of the formula I,

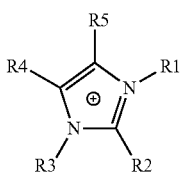

where

R1 is an organic radical having from 1 to 20 carbon atoms and R2, R3, R4 and R5 are each an H atom or an organic radical having from 1 to 20 carbon atoms.

In formula I, preference is given to R1 and R3 each being, independently of one another, an organic radical having from 1 to 10 carbon atoms. In particular, R1 and R3 are each an aliphatic radical, in particular an aliphatic radical without further heteroatoms, e.g. an alkyl group.

Particular preference is given to R1 and R3 each being, independently of one another, a C1-C10- or C1-C4-alkyl group. In a particular embodiment, R1 and R3 are identical and are, in particular, identical C1-C10- or C1-C4-alkyl groups.

In formula I, preference is given to R2, R4 and R5 each being, independently of one another, an H atom or an organic radical having from 1 to 10 carbon atoms; in particular, R2, R4 and R5 are each an H atom or an aliphatic radical. Particular preference is given to R2, R4 and R5 each being, independently of one another, an H atom or an alkyl group; in particular, R2, R4 and R5 are each, independently of one another, an H atom or a C1-C4-alkyl group. Very particular preference is given to R2, R4 and R5 each being an H atom.

The Anion Y⁻

The starting salt K⁺Y⁻ comprises the organic anion Y⁻.

Y⁻ is an organic anion having a carboxylate, sulfonate or sulfate group.

The anion Y⁻ preferably comprises a total of at least 2, in particular at least 4, particularly preferably at least 6, carbon atoms. In general, Y⁻ comprises not more than 30, in particular not more than 20, carbon atoms. In a preferred embodiment, Y⁻ comprises no further heteroatoms apart from the oxygen atoms and sulfur atoms in the carboxylate, sulfonate or sulfate groups. In particular, the anion Y⁻ comprises an anionic group selected from among a carboxylate group, a sulfonate group and a sulfate group and in addition a hydrocarbon radical without further heteroatoms or functional groups.

Suitable anions having a sulfate group are, in particular, anions of the formula $R_a$—O—$SO_3^-$, where $R_a$ is a C2-C20-alkyl group, preferably a C4-C20-alkyl group, particularly preferably a C6-C20-alkyl group.

Suitable anions having a sulfonate group are, in particular, anions of the formula $R_b$—$SO_3^-$, where $R_b$ is a C2-C20-alkyl group, preferably a C4-C20-alkyl group, particularly preferably a C6-C20-alkyl group.

The anion Y⁻ is preferably an anion having a carboxylate group.

As carboxylates of this type, particular mention may be made of organic compounds having from 1 to 20 carbon atoms and comprising a carboxylate group.

The carboxylates can be either aliphatic or aromatic carboxylates, where aromatic carboxylates are carboxylates comprising aromatic groups. Particular preference is given to aliphatic or aromatic carboxylates which, apart from the oxygen atoms of the carboxylate group, comprise no further heteroatoms or at most one or two hydroxyl groups, carbonyl groups or ether groups. Examples of the latter are hydroxycarboxylates or ketocarboxylates.

Examples of carboxylates having such further heteroatoms are the carboxylates of glycolic acid, furandicarboxylic acid, levulinic acid (4-oxopentanoic acid).

Particular preference is given to aliphatic or aromatic carboxylates which, apart from the oxygen atoms of the carboxylate group, comprise no further heteroatoms, e.g. the carboxylates of alkane carboxylic acids, alkenecarboxylic acids, alkynecarboxylic acids, alkadienecarboxylic acids, alkatrienecarboxylic acids, benzoic acid or phenylacetic acid. Suitable carboxylates of alkanecarboxylic acids, alkenecarboxylic acids and alkadienecarboxylic acids are also known as fatty acid carboxylates.

Very particular preference is given to C1-C20-alkanoates (carboxylates of alkanecarboxylic acids, in particular C1-C16-alkanoates. Particular mention may be made of the carboxylates of formic acid (C1-carboxylic acid), acetic acid (C2-carboxylic acid), propionic acid (C3-carboxylic acid), n-butyric acid (C4-carboxylic acid), n-valeric acid (C5-carboxylic acid), n-caproic acid (C6-carboxylic acid) n-caprylic acid (C8-carboxylic acid, octanoic acid), n-capric acid (C10-carboxylic acid, decanoic acid), lauric acid (C12-carboxylic acid, dodecanoic acid), palmitic acid (C16-carboxylic acid, hexadecanoic acid) or stearic acid (C18-carboxylic acid). In a particular embodiment, the anions of the salts are carboxylates of C6-C20-alkanecarboxylic acids, i.e. C6-C20-alkanoates. Particular mention may be made of C6-C14-alkanoates and in a particular embodiment C8-C12-alkanoates.

Examples of starting salts K⁺Y⁻ are:

1-ethyl-3-methylimidazolium octanoate,
1-methyl-3-methylimidazolium octanoate,
1-ethyl-3-ethylimidazolium octanoate,
1-ethyl-3-methylimidazolium ethylhexanoate,
1-methyl-3-methylimidazolium ethylhexanoate,
1-ethyl-3-ethylimidazolium ethylhexanoate,
1-ethyl-3-methylimidazolium isononanoate,
1-methyl-3-methylimidazolium isononanoate,
1-ethyl-3-ethylimidazolium isononanoate.

Particular preference is given to imidazolium salts having an imidazolium cation in which R1 and R3 are identical (see above) and a C6-C20-alkanoate (or C6-C14- or C8-C12-alkanoate) as anion.

The Acid HX

The starting salt K⁺Y⁻ is reacted with a hydrogen acid HX whose $pK_a$ is less than the $pK_a$ of the hydrogen acid HY. HY is the hydrogen acid corresponding to the above anions Y⁻.

Suitable acids HX can, for example, be selected from among the acids:

HCl, HBr, $HBF_4$, $H_3C$—COOH, HCOOH, $H_3C$—O—$SO_3H$, $H_3C$—$SO_3H$, $F_3C$—O—$SO_3H$, $HPF_6$, $CH_3$—$CH_2$—COOH, HSCN, $H_2SO_3$, $HNO_3$, $HClO_4$.

In a preferred embodiment, the solubility of HX in water is greater than the solubility of HY in water.

The reaction can, for example, be carried out at room temperature or else at elevated temperature (e.g. in the case of ionic liquids having a melting point above room temperature). Preference is given to a reaction under normal conditions, in particular at from 15 to 30° C. and atmospheric pressure.

The acid HX is added to the starting salt K⁺Y⁻. Both HX and the starting salt K⁺Y⁻ can be used in excess. The molar ratio of HX to starting salt K⁺Y⁻ can be, for example, from 0.1:1 to 1:0.1. Since the reaction is equimolar, a molar ratio of from 0.8:1 to 1:0.8 is preferred in order to avoid an excessively large excess of an unreacted compound.

Solvents can be concomitantly used when carrying out the reaction.

The reaction is preferably carried out in the presence of a solvent in which the salt $K^+X^-$ formed is soluble. In particular, the solvent is water or a hydrophilic organic solvent which is at least partially homogeneously miscible with water or a mixture thereof (hereinafter referred to collectively as aqueous solvent).

As hydrophilic solvents of this type, mention may be made by way of example of aliphatic alcohols or ethers having a maximum of 4 carbon atoms, e.g. methanol, ethanol, methyl ethyl ether or tetrahydrofuran. Suitable hydrophilic solvents have a solubility in water of at least 50 gram (g), preferably at least 100 g, in particular at least 200 g, in one liter of water (at 21° C., 1 bar). In a preferred embodiment, the hydrophilic solvent is miscible with water in any ratio (21° C., 1 bar).

Preference is given to water as a solvent.

In the reaction, concomitant use can additionally be made of a hydrophobic organic solvent in which the HY formed is soluble. Such solvents are, in particular, organic solvents which are immiscible or sparingly miscible with water. Suitable hydrophobic solvents of this type have a solubility in water of less than 200 g, in particular less than 100 g, particularly preferably less than 50 g, per liter of water (21° C., 1 bar). Mention may be made by way of example of methyl tert-butyl ether (MTBE) and in particular hydrocarbons such as alkanes, e.g. heptane, mixtures of hydrocarbons, e.g. petroleum spirit.

The aqueous solvent and the hydrophobic solvent are immiscible or only sparingly miscible. They form two separate liquid phases.

In a preferred embodiment, the reaction is carried out in the presence of an aqueous solvent. After the reaction, two liquid phases are formed: the solution of $K^+ X^-$ in the aqueous solvent and, as a separate organic phase, the acid HY.

In a likewise preferred embodiment, the reaction is carried out in the presence of both an aqueous solvent and a hydrophobic solvent. In this case, two separate liquid phases are again formed after the reaction: the solution of $K^+X^-$ in the aqueous solvent and, as a separate organic phase, the solution of HY in the hydrophobic solvent.

Preference is given to a process in which a starting salt $K^+Y^-$ having the cations $K^+$ mentioned above as preferred and/or the anions $Y^-$ mentioned above is preferred, particularly preferably an imidazolium C6-C20-alkanoate, is reacted with an acid HX, where HX is one of the abovementioned acids.

Overall Process for Preparing Imidazolium Salts

The process of the invention is, as indicated above, suitable for preparing imidazolium salts having a different anion.

The process of the invention can, in particular, follow, as a further process step, the preparation of imidazolium salts.

The preparation of imidazolium salts can be carried out in a process step as is known from WO 91/14678 and WO 2009/074535.

Salts $K^+ X^-$, where $K^+$ is an imidazolium cation of the formula I, in which R1 and R3 are each, independently of one another, an organic radical (i.e. R3 is not H) and $X^-$ is an anion, can therefore be prepared by a process in which a) an imidazolium salt $K^+Y^-$ is firstly prepared by reaction of an α-dicarbonyl compound, an aldehyde, an amine and the hydrogen acid HY and b) the imidazolium salt $K^+Y^-$ obtained in this way is reacted with a hydrogen acid HX whose $pK_a$ is less than the $pK_a$ of the hydrogen acid HY and after the reaction, the salt $K^+X^-$ obtained and the hydrogen acid HY obtained are present in separate liquid phases.

The variables $K^+Y^-$, $K^+X^-$, HX and HY have the meanings and preferred meanings given above.

Imidazolium carboxylates $K^+Y^-$ in which $Y^-$ is an anion having a carboxylate group can be prepared particularly readily by this process in step a). As regards preferred anions having a carboxylate group, what has been said above applies.

In step a), the starting compounds are selected according to the desired radicals R1 to R5 in formula I.

The α-dicarbonyl compound is preferably a compound of the formula II

R4-CO—CO—R5, where R4 and R5 are as defined above.

The compound is particularly preferably glyoxal.

The aldehyde is, in particular, an aldehyde of the formula R2-CHO, where R2 is as defined above. Particular preference is given to formaldehyde; the formaldehyde can also be used in the form of compounds which liberate formaldehyde, e.g. paraformaldehyde or trioxane.

The amines are, in particular, primary amines of the type R—$NH_2$. The radical R corresponds to the radicals R1 and R3 of the imidazolium salts obtained. When a defined primary amine is used, an imidazolium salt in which the radicals R1 and R3 are identical is obtained. If a mixture of amines (e.g. a mixture of R'—$NH_2$ and R"—$NH_2$) is used, a mixture of imidazolium salts (a mixture of salts having R1 and R3=R', R1 and R3=R" and salts having R1=R' and R3=R") is obtained.

The hydrogen acid is the hydrogen acid of the anion $Y^-$, preferably an alkanecarboxylic acid, in particular a C6-20-alkanecarboxylic acid, e.g. a C6-C14-alkanecarboxylic acid.

Carrying Out the Process

The reaction of the starting compounds can be carried out in a suitable solvent, preferably in water, a water-miscible solvent or mixtures thereof.

As water-miscible solvents, mention may be made, in particular, of protic solvents, preferably aliphatic alcohols or ethers having a maximum of 4 carbon atoms, e.g. methanol, ethanol, methyl ethyl ether, tetrahydrofuran. Suitable protic solvents are miscible with water in any ratio (at 1 bar, 21° C.).

The reaction is preferably carried out in water or mixtures of water with the above protic solvents. The reaction is particularly preferably carried out in water.

The reaction of the starting components can be carried out at atmospheric pressure and, for example, temperatures of from 5 to 100° C., in particular from 5 to 50° C., particularly preferably from 10 to 40° C.

The imidazolium salts $K^+Y^-$ can be separated off from the product mixture obtained. When the anion $Y^-$ is a compound having a carboxylate group, this can be effected very simply by means of a molecular distillation as described for imidazolium carboxylates in WO 2009/027250.

This is then followed in process step b) by the desired anion exchange. This can be carried out as described above.

The process of the invention is a simple process for preparing ionic liquids, in particular imidazolium salts having a different anion. In particular, imidazolium salts $K^+X^-$ can be prepared in only two stages by reaction of the starting compounds (α-dicarbonyl compound, aldehyde, amine, HY) to form $K^+Y^-$ and a subsequent anion exchange with an acid HX.

EXAMPLES

Example 1

Preparation of 1-ethyl-3-ethylimidazolium chloride
(1,3-EEIM chloride)

Reaction Equation:

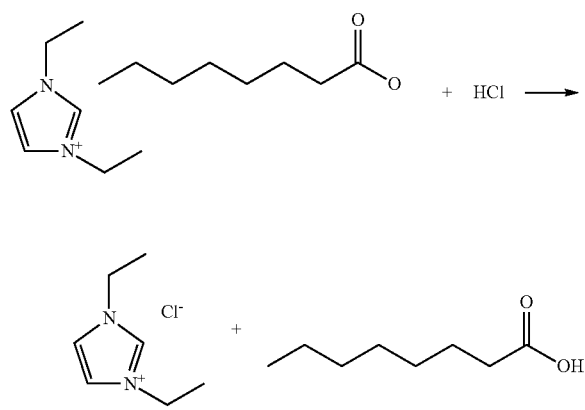

Molecular Weights 1,3-EEIM octanoate: 268.39 g/mol
HCl: 36.45 g/mol
1,3-EEIM chloride: 160.61 g/mol
Octanoic acid: 144.24 g/mol
Stirring speeds: 250 rpm
Apparatus: 5 l separating funnel, half-moon stirrer
Batch:

| | | Substance | |
|---|---|---|---|
| 2784 g | 10.37 mol | 1,3-diethylimidazolium octanoate | |
| 1000 g | 55.52 mol | water | |
| 1058 g | 10.74 mol | hydrochloric acid 37% strength | 1.04 eq based on EEIM octanoate |

Procedure:

1,3-EEIM octanoate and water were placed in the separating funnel. The hydrochloric acid was added while stirring. A white mist was formed and the mixture became hot. Stirring was continued for another 10 minutes until the two resulting phases had separated cleanly.

The upper phase was the organic phase and comprised octanoic acid.

The lower phase was the aqueous phase and comprised the aqueous solution of the imidazolium chloride formed.

The lower phase comprised only 0.55% by weight of octanoate (determined by gas chromatography).

Example 2

Preparation of 1,3-EEIM formate

Reaction Equation:

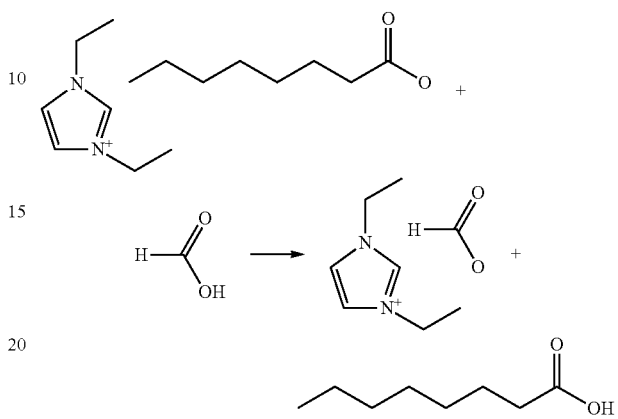

Molecular Weights 1,3-EEIM octanoate: 268.39 g/mol
Formic acid: 46.03 g/mol
1,3-EEIM formate: 170.18 g/mol
Octanoic acid: 144.24 g/mol
Apparatus: 5 l separating funnel
Batch:

| | | Substance |
|---|---|---|
| 936.7 g | 3.49 mol | 1,3-diethylimidazolium octanoate |
| 1700 g | | water |
| 1000 ml | | MTBE |
| 161.0 g | 3.50 mol | corresponding to 189.4 g of 85% strength formic acid |

Procedure:

Methyl tert-butyl ether (MTBE), water, EEIM octanoate and formic acid were placed in a 5 l separating funnel and shaken for about 5 minutes. The emulsion obtained was then allowed to stand for about 10 minutes. 2 sharply separated phases were formed.

The upper phase was the organic phase and comprised the solution of octanoic acid in MTBE. The lower aqueous phase was separated off. The EEIM formate formed was present in this phase. No octanoate could be detected by gas chromatography in the lower phase. (Detection limit: 0.01%).

The mass of the lower phase was 2312.5 g (theory: 595.74 g of EEIM formate+1728.4 g of $H_2O$=2324.2 g).

The invention claimed is:

1. A process for preparing salts $K^+ X^-$, where $K^+$ is an organic cation and $X^-$ is an anion, by anion exchange, wherein
   a salt $K^+ Y^-$, where $K^+$ is as defined above and $Y^-$ is an organic anion having a carboxylate, sulfonate or sulfate group, is used as starting material and
   $K^+ Y^-$ is reacted with a hydrogen acid HX whose pKa is less than the pKa of the hydrogen acid HY and
   after the reaction, the salt $K^+ X^-$ obtained and the hydrogen acid HY obtained are present in separate liquid phases.

2. The process according to claim 1, wherein $K^+$ is an organic cation having a heterocyclic ring system and at least one nitrogen atom as constituent of the ring system.

3. The process according to either claim 1 or 2, wherein $K^+$ is an imidazolium cation of the formula I,

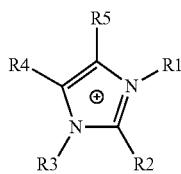

where
R1 is an organic radical having from 1 to 20 carbon atoms and
R2, R3, R4 and R5 are each an H atom or an organic radical having from 1 to 20 carbon atoms.

4. The process according to any of claims 1, wherein $K^+$ is an imidazolium cation of the formula I in which R1 and R3 are identical and are each a C1-C10-alkyl group.

5. The process according to any of claims 1, wherein $Y^-$ is a C6-C20-alkanoate.

6. The process according to any of claims 1, wherein HX is selected from among HCl, HBr, $HBF_4$, $H_3C$—COOH, HCOOH, $H_3C$—O—$SO_3H$, $H_3C$—$SO_3H$, $F_3C$—O—$SO_3H$, $HPF_6$, $CH_3$—$CH_2$—COOH, HSCN, $H_2SO_3$, $HNO_3$, $HClO_4$.

7. The process according to any of claims 1, wherein the solubility of HX in water is greater than the solubility of HY in water.

8. The process according to any of claims 1, wherein the reaction is carried out in the presence of a solvent in which the salt $K^+ X^-$ formed is soluble.

9. The process according to claim 8, wherein the solvent is water.

10. The process according to any of claims 1, wherein the reaction is carried out in the presence of an organic solvent in which the HY formed is soluble.

11. The process according to any of claims 1, wherein the reaction is carried out in the presence of a solvent in which the salt $K^+ X^-$ formed is soluble and in the presence of an organic solvent in which the HY formed is soluble.

12. A process for preparing imidazolium salts $K^+ X^-$, where $K^+$ is a 1,3-disubstituted imidazolium cation and $X^-$ is an anion, wherein
a) an imidazolium salt $K^+Y^-$ is firstly prepared by reaction of an α-dicarbonyl compound, an aldehyde, an amine and the hydrogen acid HY, wherein Y is an organic anion having a carboxylate, sulfonate or sulfate group, and
b) the imidazolium salt $K^+ Y^-$ obtained in this way is reacted with a hydrogen acid HX whose pKa is less than the pKa of the hydrogen acid HY and after the reaction, the salt $K^+ X^-$ obtained and the hydrogen acid HY obtained are present in separate liquid phases.

13. The process according to claim 10, wherein the organic solvent is a hydrophobic solvent having a solubility in water of less than 200 g per liter of water at 21° C. and 1 bar.

14. The process according to claim 11, wherein the organic solvent is a hydrophobic solvent having a solubility in water of less than 200 g per liter of water at 21° C. and 1 bar.

15. The process according to claim 13, wherein the hydrophobic solvent is methyl tert-butyl ether.

16. The process according to claim 14, wherein the hydrophobic solvent is methyl tert-butyl ether.

* * * * *